US00PP09243P

United States Patent [19]

Barbour

[11] Patent Number: Plant 9,243

[45] Date of Patent: Aug. 15, 1995

[54] *MAGNOLIA GRANDIFLORA* NAMED 'MGTIG'

[75] Inventor: John Barbour, Monroe, Ga.

[73] Assignee: Athena Trees, Inc., Monroe, Ga.

[21] Appl. No.: 313,005

[22] Filed: Sep. 27, 1994

[51] Int. Cl.[6] ..... A01H 5/00
[52] U.S. Cl. ..... Plt./53.5
[58] Field of Search ..... Plt. 53.5

*Primary Examiner*—James R. Feyrer
*Attorney, Agent, or Firm*—Klarquist Sparkman Campbell Leigh & Whinston

[57] ABSTRACT

A new variety of *Magnolia grandiflora* is characterized by its candle flame shaped, compact growth habit and mature leaves which have a lustrous dark green upper surface and which are of a convex shape.

1 Drawing Sheet

The present invention relates to a new and distinct variety of *Magnolia grandiflora,* commonly called Southern magnolia. I have given my plant the varietal name 'Mgtig'.

Southern magnolias are extremely variable in growth habit, leaf and flowering characteristics. Seedling-grown material is often open and unkempt, and these characteristics typically limit the attractiveness of the plants in landscaping applications.

The parent tree of the new variety was discovered as it was growing in a cultivated area at a residence located in Campton, Ga. This tree was planted at this residence as a two-year old container-grown seedling of unknown parentage and has not been transplanted. My attention was drawn to the plant due to its having a superior dense growth habit and foliage characteristics. Asexual reproduction of the new variety at my direction from cuttings and observation of the resulting progeny growing in a nursery in Monroe, Ga., has proven the characteristics of my new variety to be fixed. Furthermore, these observations have confirmed that my new variety represents a new and improved variety of magnolia tree, as particularly evidenced by the following unique combination of characteristics, which have proven firmly fixed, are outstanding therein, and which distinguish it from all of the varieties of this species of which I am aware:

1. Dense candle flame shaped compact habit; and
2. Mature leaves which have an upper surface which is a lustrous dark green and wherein such leaves are of a convex shape.

OVERALL DESCRIPTION OF THE VARIETY

'Mgtig' is an attractive plant that exhibits a rapid rate of growth compared to other varieties of Southern magnolia, particularly in nursery conditions. Three-year old plants growing in a nursery in Monroe, Ga., typically have grown to a height 7 to 8 feet and a width of 4 feet while maintaining a dense framework of branches and leaves. When seventeen years old, the parent tree was 22 feet high and 11 feet wide. The growth habit is dense and of a desirable candle flame shape. The dense habit is due primarily to closely spaced nodes and thus leaves, and also to greater multiple breaks from new growth shoots from each season. The leaves, which are typically somewhat smaller than other varieties, are uniquely convex and have lustrous dark green upper surfaces and light green under surfaces. Flowers and fruits of my new variety are somewhat smaller than other varieties.

The new variety has been asexually reproduced from July–August, firm wood, 4 to 6 inch long cuttings that are treated with 10,000 ppm naphtheneacetic acid dissolved in 50% alcohol. Cuttings are placed in horticultural grade perlite in 4 inch deep flats on a greenhouse bench under intermittent mist. Rooting occurs in 6 to 10 weeks at 30 to 50 percent. All plants produced have been identical insofar as observable to the parent plant. The plant is therefore relatively easy to propagate in comparison to many other Southern magnolia varieties.

BRIEF DESCRIPTION OF THE DRAWING

The accompanying photographs depict the color of the blooms and leaves of my new variety and also the growth habit thereof.

DETAILED BOTANICAL DESCRIPTION

Figure 1:
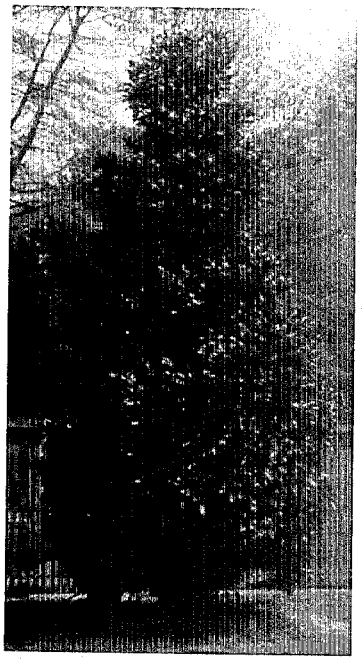
FIG. 1 is a photograph of the parent tree of my new variety which shows the overall growth habit of the tree.
Figure 2:
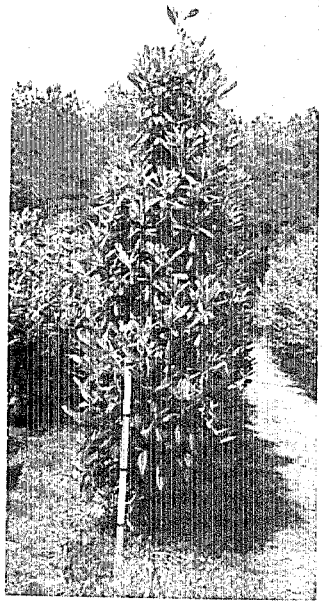
FIG. 2 illustrates one of the progeny of the new variety growing in a nursery row.
Figure 3:
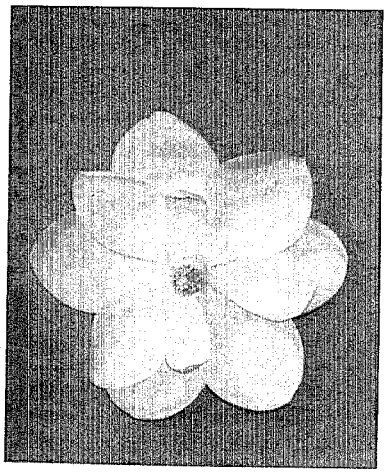
FIG. 3 illustrates a flower of the new variety.
Figure 4:
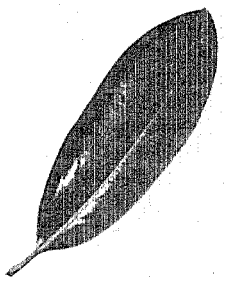
FIG. 4 shows a mature leaf from a tree of the new variety.

My new variety of Souther magnolia is vigorous and characterized by rapid growth rate, particularly under nursery conditions, where three-year old plants growing in Monroe, Ga., have grown 7 to 8 feet high and 4 feet wide while maintaining a dense framework of branches and leaves. The habit is compact, dense and is a candle flame shape in outline. The new variety's density results from the more closely spaced nodes (thus leaves) and greater multiple breaks from the new shoot growth of the season. The leaves are somewhat smaller than those of typical Southern magnolia trees, uniquely convex, lustrous dark green above and light green beneath. Flowers and fruits of my new variety are slightly smaller than typical.

DETAILED BOTANICAL DESCRIPTION

The following is a detailed description of my new variety of Southern magnolia tree, with color terminology in accordance with The Royal Horticultural Society Colour Chart (hereinafter R.H.S.), published by The Royal Horticultural Society of London.

Parentage: Seedling of unknown parentage.

Propagation: Holds to distinguishing characteristics through succeeding propagation by rooted cuttings.

Locality where grown and observed: Monroe, Ga.

Tree: Strong upright tree with a compact, candle flame shaped growth habit. The plant has a straight single leader with secondary branches that ascend at an angle of about 30 degrees from leader. Internode length ranges from about $\frac{3}{4}$ to 2 inches to produce a dense foliage canopy.

Stems:

*Strength.*—First year stems are less stout than typical of the species and average about 3/16 to $\frac{1}{3}$ inch in diameter.

*Pubescent.*—New stems are covered with a fine brown pubescence that disappears with maturity. Second year and older stems are completely glabrous.

*Color.*—First year stems are a yellow-green (like RHS 144A), second year stems are green (like RHS 143A), and third year stems develop a gray-orange color (like RHS 165B) and a smooth bark.

Vigor: Vigorous, being faster growing than other varieties of Southern magnolia trees. Three-year old plants growing in Monroe, Ga., under nursery conditions have grown 7 to 8 feet high and 4 feet wide, while maintaing a dense framework of branches and leaves.

Foliage:

*Size.*—Leaves average about 5.8 inches long by about 2.4 inches wide.

*Shape.*—The mature leaves are elliptic to slightly obovate-oblong and convex.

*Apex.*—Acute to acuminate.

*Base.*—Wedge shaped.

*Margin.*—Entire.

*Color.*—The upper mature leaf surface is lustrous dark green (like RHS 137A), and the lower leaf surface is a flat yellow-green (like RHS 146B). The unique combination of a convex leaf shape and high gloss distinguish this new variety from all other known Southern magnolia trees.

*Petiole.*—Average about $\frac{1}{2}$ inch long. The petioles are yellow-green (like RHS 145A).

*Pubescent.*—Mature leaves are glabrous. The green color of the leaves is maintained throughout the seasons due to the absence of brown pubescence on the underside of the leaves.

Flowers and fruits:

*Size.*—Flowers averaging about 5 to 6 inches wide and fruits averaging about $2\frac{1}{2}$ to 3 inches long. These sizes are somewhat smaller than is typical for the species.

*Age when flowers observed.*—Four-year old nursery grown plants growing in Monroe, Ga., have been observed to flower and produce fruits. In comparison, typical seed-grown Southern magnolia trees take five to ten years to produce flowers.

*Other characteristics of flowers and fruits*—Insofar as they have been observed, otherwise the flowers and fruits of the new variety are typical for the species.

Ultimate tree size: Unknown at this time, although original tree at seventeen years of age was 22 feet high.

I claim:

1. A new and distinct variety of Southern Magnolia tree as herein described and illustrated, primarily characterized by a candle flame shaped compact growth habit and mature leaves with an upper surface which is a lustrous dark green and which are of a convex shape.

* * * * *